(12) United States Patent
Shukla

(10) Patent No.: US 9,170,210 B2
(45) Date of Patent: Oct. 27, 2015

(54) TECHNIQUE FOR CYLINDRICAL PART INNER SURFACE INSPECTION

(75) Inventor: Salil Shukla, Farmington Hills, MI (US)

(73) Assignee: Federal-Mogul Corporation, Southfield, MI (US)

( * ) Notice: Subject to any disclaimer, the term of this patent is extended or adjusted under 35 U.S.C. 154(b) by 369 days.

(21) Appl. No.: 13/153,897

(22) Filed: Jun. 6, 2011

(65) Prior Publication Data

US 2012/0307040 A1    Dec. 6, 2012

(51) Int. Cl.
*H04N 7/18* (2006.01)
*G01N 21/954* (2006.01)

(52) U.S. Cl.
CPC .................. *G01N 21/954* (2013.01)

(58) Field of Classification Search
CPC ......... G01N 21/954; G03B 15/06; G06K 7/00
USPC ........................................................ 348/84
See application file for complete search history.

(56) References Cited

U.S. PATENT DOCUMENTS

| | | | | |
|---|---|---|---|---|
| 5,004,339 A | * | 4/1991 | Pryor et al. | 356/241.1 |
| 2010/0201806 A1 | * | 8/2010 | Nygaard et al. | 348/92 |
| 2010/0236578 A1 | * | 9/2010 | Noda et al. | 134/23 |

FOREIGN PATENT DOCUMENTS

| | | |
|---|---|---|
| DE | 19738827 C1 | 7/1999 |
| EP | 0987541 A1 | 3/2000 |
| JP | 57028239 A | 2/1982 |
| JP | 3226659 A | 10/1991 |
| JP | 10176994 A | 6/1998 |
| WO | 2005038446 A1 | 4/2005 |
| WO | 2005067422 A2 | 7/2005 |

OTHER PUBLICATIONS

International Search Report PCT/US2012/030817 mailed on Jul. 13, 2012.

* cited by examiner

*Primary Examiner* — Mehrdad Dastouri
*Assistant Examiner* — Nguyen Truong
(74) *Attorney, Agent, or Firm* — Robert L. Stearns; Dickinson Wright, PLLC

(57) ABSTRACT

A system and method for inspecting inner surfaces (22) of cylindrical parts (20) includes a line scan camera (30), a pair of light emitting diodes each directing light toward the inner surface (22), and a mirror (36) disposed in the cylindrical part (20) at a 45 degree angle relative to the inner surface (22). The camera (30) and mirror (36) remain in a fixed position while the cylindrical part (20) rotates continuously about a center axis (A) and the images are acquired. The cylindrical part (20) is then moved laterally along the center axis (A) and the images are again acquired as the cylindrical part (20) rotates about the center axis (A). An unwrapped display of the inner surface (22) is generated and used to automatically identify defects (24) on the inner surface (22).

23 Claims, 2 Drawing Sheets

TECHNIQUE FOR CYLINDRICAL PART INNER SURFACE INSPECTION

BACKGROUND OF THE INVENTION

1. Field of the Invention

This invention relates to a system and method for inspecting inner surfaces of cylindrical parts, such as cylinder liners for internal combustion engines.

2. Description of the Prior Art

Cylindrical parts, such as heavy-duty liners for internal combustion engines, are inspected manually by humans for subtle defects, such as cracks and porosity defects, in an effort to avoid shipping defective parts to a customer. The costs associated with this manual inspection process add up to hundreds of thousands of dollars each year. Further, a single human inspector is typically required to inspect thousands of cylindrical parts each day. The cylindrical parts are heavy, and subtle defects, such as those less than 200 microns, as well as defects located near the center of the cylindrical parts, are hardly visible to the naked eye. Thus, chances of overlooking defects due to physical or mental fatigue, or inability to see the defects, and consequently shipping a defecting part to a customer are high.

In attempt to reduce human error, automated surface inspection techniques have been developed. An example of an automated technique is disclosed in U.S. Patent Application Publication No. 2007/0132990. Machine vision techniques have also been employed for inspection of cylindrical parts, including inspection of both the inner and external surface of the cylindrical part. However, the techniques used to inspect the inner surface either require the camera to be disposed inside the cylindrical part or require a conical mirror. The first technique requires on-axis lighting and the camera and lens are subject to size restraints. Thus, images acquired typically have low resolution and distortion. In addition, the position of the camera and light source must be adjusted numerous times to acquire images of the entire inner surface, which is burdensome and time consuming. The second technique requires an appropriately sized conical mirror for every cylindrical part inspected. Further, the conical mirror typically causes distortion in the image due to compressed pixels.

SUMMARY OF THE INVENTION

The invention provides an improved system for inspecting inner surfaces of cylindrical parts. Each cylindrical part includes an inner surface extending circumferentially around a center axis and presenting a bore. A camera is disposed outwardly of and axially aligned with the center axis of the cylindrical part for acquiring images of the inner surface. The camera is a line scan camera and each of the images are one dimension. A light source is disposed adjacent to the camera for directing light to the inner surface of the cylindrical part. A mirror is disposed in the bore of the cylindrical part at a predetermined and fixed position along the center axis, and at a 45 degree angle relative to the inner surface. The mirror reflects the light from the light source to the inner surface and from the inner surface to the camera.

The invention also provides a method for inspecting an inner surface of a cylindrical part. The method comprises the steps of providing a plurality of cylindrical parts each including an inner surface extending circumferentially around a center axis; and disposing a mirror in one of the cylindrical parts at a predetermined and fixed position along the center axis and at a 45 degree angle relative to the inner surface. The method also includes directing light to the inner surface of the cylindrical part; reflecting the light between the mirror and the inner surface; and acquiring a plurality of images each being one dimension of the inner surface of the cylindrical part.

The system and method of the present invention provides a reliable, cost efficient way to identify defects on the inner surfaces. High resolution imagery of the inner surface with minimal image distortion is provided. Further, a single mirror can be used to inspect cylindrical parts of different sizes, and the position of the camera and the light source can remain fixed while inspecting the entire cylindrical part and while inspecting numerous cylindrical parts of the same size. The images can be used to automatically identify defects, including defects in the 200 micron range or less. Thus, when using the inventive system and method, the chances of overlooking defects and sending defective cylindrical parts to a customer are significantly reduced, compared to the prior art. Further, the inspection time, including part handling time, for each cylindrical part is typically about 10 seconds or less, which is faster than the prior art.

BRIEF DESCRIPTION OF THE DRAWINGS

Other advantages of the present invention will be readily appreciated, as the same becomes better understood by reference to the following detailed description when considered in connection with the accompanying drawings wherein.

DETAILED DESCRIPTION OF THE ENABLING EMBODIMENTS

Figure 1A:
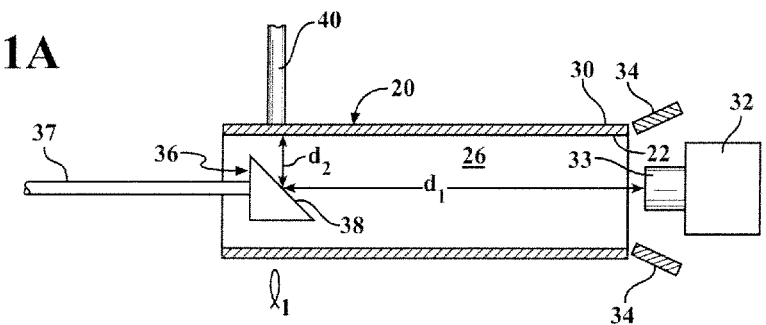
FIGS. 1A-1C are schematic views of a system and method for inspecting an inner surface of a cylindrical part according to one aspect of the present invention.
Figure 1B:
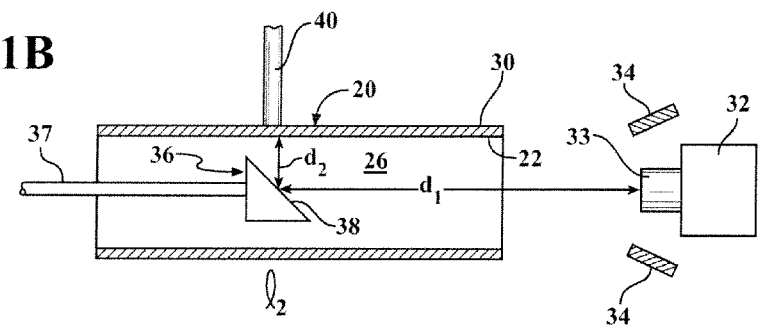
Figure 1C:
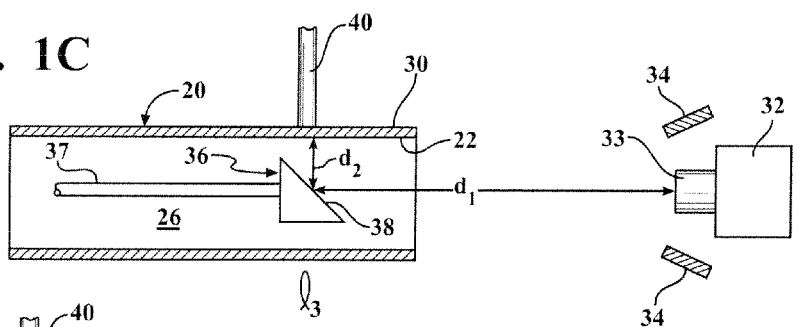

Referring to the Figures, a system and method for inspecting cylindrical parts 20 is generally shown in schematic drawings of FIGS. 1A-1C.

Figure 3:
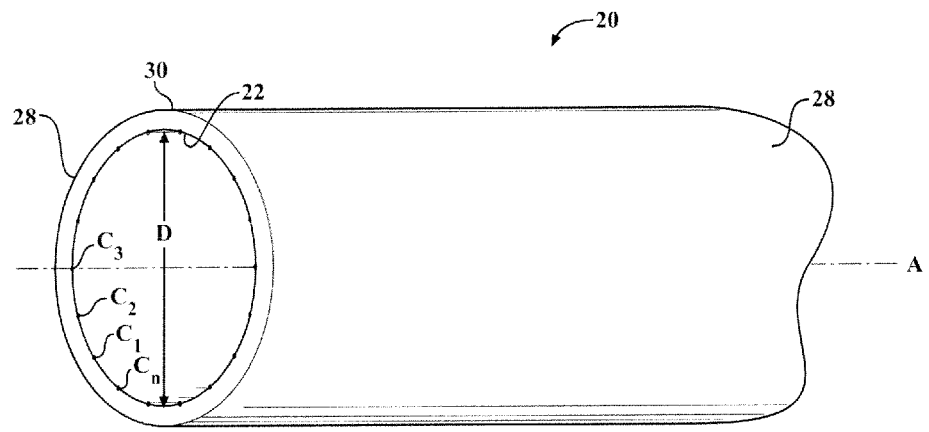
FIG. 3 is a perspective view of an exemplary cylindrical part inspected using the system and method of the present invention.

The system includes the plurality of cylindrical parts 20, such as cylinder liners for internal combustion engines. The cylindrical parts 20 are typically in the possession of a manufacture and are being prepared for shipping to a customer. The manufacturer will employ the system and method to inspect inner surfaces 22 of the cylindrical parts 20 for defects 24 or flaws prior to shipping the cylindrical parts 20 to the customer. Each of the cylindrical parts 20 includes the inner surface 22 extending circumferentially around a center axis A and presenting a bore 26 between opposite ends 28. The cylindrical part 20 also includes an outer surface 30 facing opposite the inner surface 22. The inner surface 22 of each cylindrical part 20 presents an inner diameter D between the opposite ends 28, as shown in FIG. 3.

Figure 2:
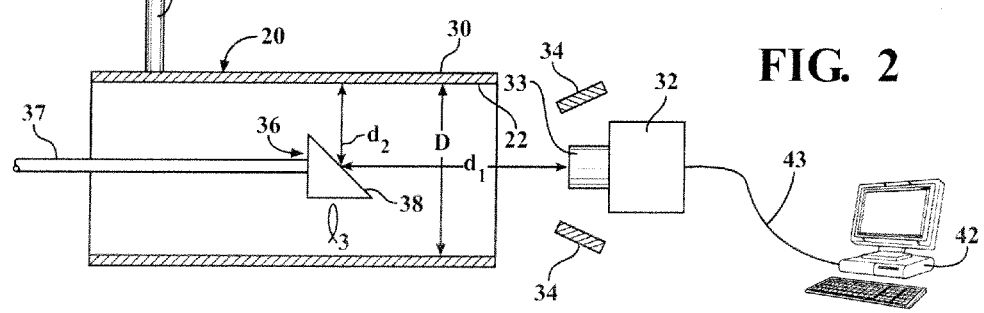
FIG. 2 is a schematic view of another embodiment of the system and method for inspecting an inner surface of a cylindrical part.

The system includes a camera 32 for acquiring images of the inner surfaces 22 of the cylindrical parts 20, and the images are used to identify any defects 24 on the inner surfaces 22. The camera 32 includes a lens 33 facing the bore 26 of the cylindrical part 22 for acquiring the images. The camera 32 acquires the images of one cylindrical part 20 at a time. The camera 32 is disposed in a predetermined position outwardly of one of the ends 28 of the cylindrical part 20, as shown in FIG. 1A. The camera 32 is also axially aligned with the center axis A of the cylindrical part 20. The position of the camera 32 along the center axis A remains fixed while the images of the cylindrical part 20 are acquired. The camera 32 also remains in the same, fixed position when inspecting cylindrical parts 20 having the same inner diameter D. However, the position of the camera 32 along the center axis A is typically adjusted longitudinally prior to acquiring images of other cylindrical parts 20 having greater or smaller inner diameters D, as shown in FIG. 2.

The camera 32 is preferably a high resolution line scan camera, and each of the images acquired are one-dimension. The images can be referred to as line images because each image acquired is a line of single pixels. The pixels of each line image are disposed one directly after the other. Each of the line images shows a small portion of the inner surface 22 of the cylindrical part 20. The camera 32 acquires each of the line images at a predetermined circumferential location $c_1$, $c_2$, $c_3$, ... $c_n$ along the circumference of the inner surface 22, as shown in FIG. 3. For example, one line image is acquired at $c_1$, another line image is acquired at $c_2$, another at $c_3$, and so on around the inner surface 22. Each pixel is square and each line image accurately reflects the dimension of the inner surface 22. The line images are not stretched or compressed. In one preferred embodiment, the camera (32) includes a charge-coupled device (CCD) for acquiring the images.

In one embodiment, the line scan camera 32 is 1K, which means the camera 32 can acquire images of 1K, or 1,000 pixels. The resolution provided by the camera 32 will change depending on the field of view of the lens 33 or the surface area under observation. For example, if the camera 32 is 1K and has a field of view of 100 millimeters, then the resolution provided by the camera 32 is 100 microns (100 millimeters÷1,000 pixels). Thus, when the system includes a 1K camera 32, the system can detect flaws in the 300 micron range. If the camera 32 is 16K and has a field of view of 100 millimeters, then the resolution provided by the camera 32 is 6.3 microns (100 millimeters÷ 16,000 pixels). Thus, with a 16K camera 32, the system can detect flaws in the 20 micron range. The camera 32 selected for use in the system of the present invention can be in the range of 1K to 16K, or more, depending on the size of the flaws that need to be detected.

A light source 34 is disposed between the end 28 of the cylindrical part 20 adjacent the camera 32 and the camera 32 for directing light into the bore 26 and to the inner surface 22 of the cylindrical part 20. In one embodiment, the light source 34 includes a light emitting diode directing a consistent line of light to the inner surface 22. In another embodiment, the light source 34 includes a pair of light emitting diodes opposite one another relative to the camera 32, as shown in FIGS. 1A-2. Each light emitting diode is disposed adjacent the lens 33 of the camera 32. The light source 34 preferably provides front diffused lighting to the inner surface 22.

The system also includes a mirror 36 disposed in the bore 26 of the cylindrical part 20 adjacent and spaced from the inner surface 22. The mirror 36 is disposed at a predetermined position along the center axis A of the cylindrical part 20 and can be supported by a rod 37. The mirror 36 has a mirror surface 38 facing generally toward the camera 32. The mirror surface 38 is planar and is disposed at a 45 degree angle relative to the inner surface 22 of the cylindrical part 20. The mirror 36 reflects the light from the light source 34 to the inner surface 22 and from the inner surface 22 to the camera 32 so that the camera 32 can acquire the images of the inner surface 22.

The position of the mirror 36 remains fixed while images are acquired for one of the cylindrical parts 20. The mirror 36 also remains in the same, fixed position while inspecting other cylindrical parts 20 having the same inner diameter D. However, the position of the mirror 36 along the center axis A is typically adjusted longitudinally prior to acquiring images of other cylindrical parts 20 having different inner diameters D, as shown in FIG. 2. The position of the mirror 36 relative to the camera 32 is selected so that the images acquired by the camera 32 are clear and accurate without distortion.

The mirror 36 is spaced from the camera 32 by a first distance $d_1$ and spaced from the inner surface 22 by a second distance $d_2$. However, in one embodiment, although the first distance $d_1$ and the second distance $d_2$ vary for cylindrical parts 20 having different inner diameters D, the sum of the first distance $d_1$ and the second distance $d_2$ remains fixed for all the cylindrical parts 20 inspected. For example, the sum of the first distance $d_1$ and the second distance $d_2$ of FIGS. 1A-1C are equal to the sum of the first distance $d_1$ and the second distance $d_2$ while inspecting cylindrical parts 20 having an inner diameter D of 0.01 meters is the same as the sum of the first distance $d_1$ and the second distance $d_2$ while inspecting cylindrical parts 20 having an inner diameter D of 0.05 meters. Maintaining the sum of the first distance $d_1$ and the second distance $d_2$ fixed provides consistently clear and accurate images without distortion.

The system includes an arm 40 supporting the cylindrical part 20 during inspection. The arm 40 typically engages the outer surface 30 of the cylindrical part 20 and moves the cylindrical part 20 relative to the mirror 36 and the camera 32 continuously while the camera 32 acquires the images of the inner surface 22. The arm 40 continuously rotates the cylindrical part 20 360 degrees about the center axis A. The arm 40 maintains the cylindrical part 20 in a first position longitudinally along the center axis A between the opposite ends 28, referred to as a first predetermined longitudinal position $l_1$, during the 360 degree rotation, as shown in FIG. 1A. While the cylindrical part 20 is rotating in the first longitudinal position $l_1$, images of the inner surface 22 are reflected from the mirror 36 to the camera 32, so that the camera 32 can acquire the images. The camera 32 acquires the images at the predetermined circumferential locations $c_1$, $c_2$, $c_3$ ... $c_n$ around the circumference of the inner surface 22 until images are acquired for the entire circumference of the inner surface 22 at the first predetermined longitudinal position $l_1$. The number of circumferential locations $c_1$, $c_2$, $c_3$ ... $c_n$ and number of images acquired at the first predetermined longitudinal position $l_1$ are directly proportional to the inner diameter D of the cylindrical part 20.

After acquiring images of the inner surface 22 of the cylindrical part 20 at the first predetermined longitudinal position $l_1$, the arm 40 moves the cylindrical part 20 a predetermined, fixed distance longitudinally along the center axis A to a second predetermined longitudinal position $l_2$, as shown in FIG. 1B. Next, the arm 40 continuously rotates the cylindrical part 20 360 degrees about the center axis A while maintaining the cylindrical part 20 in the second predetermined longitudinal position $l_2$. While the cylindrical part 20 is continuously rotated in the second longitudinal position $l_2$, images of the inner surface 22 are reflected from the mirror 36 to the camera 32, so that the camera 32 can acquire the images. The camera 32 acquires the images at the predetermined circumferential locations $c_1$, $c_2$, $c_3$ ... $c_n$ around the circumference of the inner surface 22 until images are acquired around the entire circumference of the inner surface 22 at the second longitudinal position $l_2$. The predetermined circumferential locations $c_1$, $c_2$, $c_3$ ... $c_n$ are the same as those at the first longitudinal position $l_1$. The number of line images acquired at the second longitudinal position $l_2$ is also directly proportional to the inner diameter D of the cylindrical part 20.

After acquiring images of the entire inner surface 22 of the cylindrical part 20 at the second longitudinal position $l_2$, the arm 40 moves the cylindrical part 20 a predetermined, fixed distance longitudinally along the center axis A to a third predetermined longitudinal position $l_3$, as shown in FIG. 1C. The arm 40 continuously rotates the cylindrical part 360 degrees about the center axis A while maintaining the cylindrical part 20 in the third longitudinal position $l_3$. While the cylindrical part 20 is continuously rotated in the third longitudinal position $l_3$, images of the inner surface 22 are reflected from the mirror 36 to the camera 32, so that the camera 32 can acquire the images. The camera 32 acquires the images at the predetermined circumferential locations $c_1, c_2, c_3 \ldots c_n$ around the circumference of the inner surface 22 until images are acquired around the entire circumference of the inner surface 22 at the third longitudinal position $l_3$. The predetermined circumferential locations $c_1, c_2, c_3 \ldots c_n$ are the same as those at the first longitudinal position $l_1$ and the second longitudinal position $l_2$. The number of images acquired at the third longitudinal position $l_3$ is also directly proportional to the inner diameter D of the cylindrical part 20.

The image acquiring, rotating, and longitudinal movement steps are repeated so that images are acquired at additional longitudinal positions $l_n$ along the inner surface 22. The images are acquired at the predetermined circumferential locations $c_1, c_2, c_3 \ldots c_n$ at each longitudinal position $l_1, l_2, l_3 \ldots l_n$. As stated above, each of the images is acquired at one of the predetermined circumferential locations $c_1, c_2, c_3 \ldots c_n$ and one of the longitudinal positions $l_1, l_2, l_3 \ldots l_n$. The steps are repeated until the images, preferably line images, are acquired for the entire inner surface 22 between the opposite ends 28 of the cylindrical part 20.

The images acquired by the line scan camera 32 have a high resolution. Further, distortion of the images is minimal because the planar mirror surface 38 at the 45 degree angle reflects the inner surface 22 without compressing the reflection, unlike a conical shaped mirror which would compress the reflection and thus the image would include compressed pixels. Further, the fixed positions of the camera 32 and mirror 36 during inspection of one of the cylindrical parts 20 allows for a high alignment accuracy, which also contributes to the high quality of the images.

The system also includes a computer 42 for combining the images of the inner surface 22, preferably line images, acquired by the camera 32. In one embodiment, the computer 42 is connected to the camera 32 by a cable 43, as shown in FIG. 2. The line images are arranged together in sequence, according to the predetermined circumferential locations $c_1, c_2, c_3 \ldots c_n$ and longitudinal positions $l_1, l_2, l_3 \ldots l_n$ to generate a high quality unwrapped display including each of the line images acquired for the inner surface 22. The images are typically arranged in the order they were acquired by the camera 32.

Figure 4:
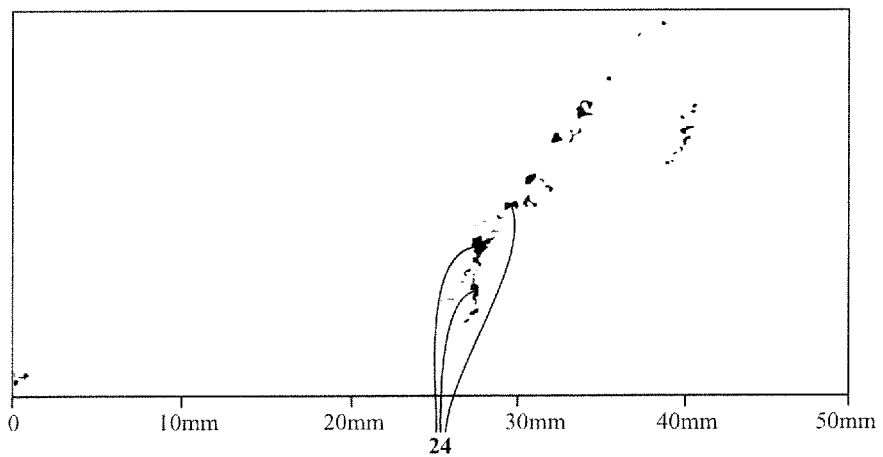
FIG. 4 is an unwrapped display of an inner surface generated according to one embodiment of the present invention.

The unwrapped display accurately portrays the dimensions and characteristics of the inner surface 22. Thus, the unwrapped display provides a clear and accurate illustration of the inner surface 22. FIG. 4 provides an example of a small portion of the unwrapped display. FIG. 4 includes a plurality of line images each acquired at a different circumferential location $c_1, c_2, c_3$ but at a single longitudinal position $l_1$. The line images of FIG. 4 are arranged together in sequence according to the circumferential locations $c_1, c_2, c_3$. Porosity defects 24 as well as machining defects or lines can be clearly identified in the portion of the unwrapped display.

In one embodiment, the computer 42 automatically identifies defects 24 on the inner surface 22 of the cylindrical part 20 using standard image processing algorithms of the images or the unwrapped display. In another embodiment, the images or the unwrapped display is manually studied for defects 24. If defects 24 on the inner surface 22 are identified, then the manufacturer will discard or repair the cylindrical part 20 before sending the cylindrical part 20 to the customer.

As stated above, all cylindrical parts 20 having the same inner diameter D are inspected while the camera 32 and mirror 36 are maintained in the predetermined, fixed position. The positions of the camera 32 and mirror 36 are adjusted longitudinally along the center axis A and relative to one another before inspecting cylindrical parts 20 having different inner diameters D or dimensions, as shown in FIG. 2. The camera 32 and the mirror 36 are adjusted to provide a clearer, more accurate image of the inner surface 22. However, as stated above, the sum of the first distance $d_1$ and the second distance $d_2$, is the same, even when inspecting cylindrical parts 20 having different inner diameters D. The position of the light source 34 can also be adjusted prior to inspecting cylindrical parts 20 of different inner diameters D and dimensions to effectively direct light toward the inner surface 22.

In one preferred embodiment, the inner surface 22 of the cylindrical part 20 is cleaned before the camera 32 acquires the images. Dirt, dust, grease, and other debris are removed from the inner surface 22 using standard cleaning methods. The unwrapped display of the clean cylindrical part 20 is of higher quality than the unwrapped display of a dirty or greasy cylindrical part 20. If the inner surface 22 is greasy or dirty, it may be difficult to distinguish actual defects 24 from dirt or flaws.

As stated above, the invention also provides a method for inspecting the inner surfaces 22 of the cylindrical parts 20. The method includes providing the plurality of cylindrical parts 20 each including the inner surface 22 extending circumferentially around the center axis A.

Next, the method includes disposing the mirror 36 in one of the cylindrical part 20 along the center axis A, and disposing the mirror 36 at a 45 degree angle relative to the inner surface 22 of the cylindrical part 20. The method also includes disposing the camera 32 adjacent to the cylindrical part 20; axially aligning the camera 32 with the center axis A of the cylindrical part 20; and fixing the sum of the distance between the camera 32 and the mirror 36 and the distance between the mirror 36 and the inner surface 22, referred to as the sum of the first distance $d_1$ and the second distance $d_2$.

The system set up includes disposing the light source 34 between the camera 32 and the cylindrical part 20; directing light from the light source 34 to the mirror 36; reflecting the light to the inner surface 22 and from the inner surface 22 to the camera 32; and acquiring the plurality of images each being one-dimension and including the line of single pixels showing a portion of the inner surface 22 of the cylindrical part 20 by the camera 32 while rotating the cylindrical part 20 360 degrees about the center axis A.

The step of acquiring the images includes acquiring the images at the predetermined circumferential locations $c_1, c_2, c_3 \ldots c_n$ around the circumference of the inner surface 22 while rotating the cylindrical part 20 360 degrees about the center axis A in the first longitudinal position $l_1$; moving the cylindrical part 20 a predetermined distance longitudinally along the center axis A to the second longitudinal position $l_2$ after acquiring the images in the first longitudinal position $l_1$; and acquiring the images at the predetermined circumferential locations $c_1, c_2, c_3 \ldots c_n$ around the circumference of the inner surface 22 while rotating the cylindrical part 20 360 degrees about the center axis A in the second longitudinal position $l_2$. The method includes repeating the acquiring, the rotating, and the moving steps until images are acquired for the entire inner surface 22 of the cylindrical part 20.

In one preferred embodiment, after acquiring each of the line images at one of the predetermined circumferential locations $c_1, c_2, c_3 \ldots c_n$ and one of the longitudinal positions $l_1, l_2, l_3 \ldots l_n$ of the inner surface 22, the method includes combining each of the line images together and arranging the line images in sequence according to the predetermined circumferential locations $c_1, c_2, c_3 \ldots c_n$ and the longitudinal positions $l_1, l_2, l_3 \ldots l_n$; and generating the unwrapped display of the inner surface 22 of the cylindrical part 20 including the arranged line images.

In one embodiment, the method includes automatically identifying defects 24 on the inner surface 22 of the cylindrical part 20 using standard image processing algorithms of the line images. The method includes repeating the steps for each of the cylindrical parts 20 having the same inner diameter D and dimensions. When inspecting cylindrical parts 20 having different inner diameters D or dimensions, the method can include adjusting the position of the camera 32 and the mirror 36 longitudinally along the center axis A and relative to one another in order to acquire clear and accurate images of the inner surface 22. However, the sum of the first distance $d_1$ and the second distance $d_2$ remains fixed. The method can also include adjusting the position of the light source 34 prior to inspecting cylindrical parts 20 of different inner diameters D and dimensions to effectively direct light toward the inner surface 22.

Finally, the method includes repeating the steps for each of the cylindrical parts 20, including generating the unwrapped display and identifying defects 24 for each of the cylindrical parts 20. In one preferred embodiment, the method includes cleaning the inner surfaces 22 of the cylindrical parts 20, prior to acquiring the images, to obtain better quality images. The method also typically includes discarding the cylindrical parts 20 including defects 24 or repairing the defects 24 in the cylindrical parts 20 before sending the cylindrical parts 20 to the customer.

Obviously, many modifications and variations of the present invention are possible in light of the above teachings and may be practiced otherwise than as specifically described while within the scope of the appended claims. These antecedent recitations should be interpreted to cover any combination in which the inventive novelty exercises its utility.

What is claimed is:

1. A system for inspecting inner surfaces of cylindrical parts, comprising:
   a plurality of cylindrical parts having different inner diameters, each of said cylindrical parts including an inner surface presenting said inner diameter and extending circumferentially around a center axis and longitudinally between opposite ends to present a bore,
   a camera with a lens for acquiring images of said inner surface while said cylindrical part rotates 360 degrees about said center axis;
   said lens of said camera being disposed outwardly of said cylindrical part;
   said lens remaining in a fixed position while acquiring said images of said inner surface and while said cylindrical part rotates 360 degrees about said center axis and moves longitudinally along said center axis;
   a light source disposed outwardly of said cylindrical part for directing light to said inner surface of said cylindrical part;
   a mirror disposed in said bore of said cylindrical part at a predetermined and fixed position along said center axis while said cylindrical part rotates 360 degrees about said center axis and moves longitudinally along said center axis and while said camera acquires said images of said inner surface;
   said mirror including a mirror surface being disposed at an angle relative to said inner surface for reflecting the light from said light source to said inner surface and from said inner surface to said lens of said camera;
   said mirror surface being disposed in a fixed position on said center axis relative to said inner surface of said cylindrical part while said cylindrical part rotates 360 degrees about said center axis and moves longitudinally along said center axis;
   said lens and said mirror surface remaining in a fixed position until said camera acquires images of the entire inner surface between said opposite ends of said cylindrical part, and
   wherein said mirror is spaced from said camera by a first distance and spaced from said inner surface by a second distance, and a sum of said first distance and said second distance is fixed while said camera acquires images of said inner surfaces of each of said cylindrical parts.

2. A system as set forth in claim 1 wherein said camera includes a charge-coupled device for acquiring said images.

3. A system as set forth in claim 1 wherein each of said images is a line of pixels.

4. A system as set forth in claim 3 wherein each of said images are acquired at a predetermined circumferential location and a predetermined longitudinal position along said inner surface; and including an unwrapped display of said inner surface including each of said images arranged according to said predetermined circumferential locations and said predetermined longitudinal positions.

5. A system as set forth in claim 1 wherein said mirror surface faces generally toward said camera and is planar.

6. A system as set forth in claim 1 including an arm supporting said cylindrical part and moving said cylindrical part relative to said mirror and said camera while said camera acquires said images.

7. A system as set forth in claim 1 wherein said camera acquires images of said inner surface of each of said cylindrical parts.

8. A system as set forth in claim 1 wherein said fixed mirror surface does not rotate around said center axis.

9. A system as set forth in claim 1 wherein said light source remains in a fixed position while said cylindrical part rotates 360 degrees about said center axis and moves longitudinally along said center axis, and said light source remains in said fixed position until said camera acquires images of the entire inner surface between said opposite ends of said cylindrical part.

10. A method for inspecting an inner surface of cylindrical parts, comprising the steps of:
   providing a plurality of cylindrical parts having different inner diameters, each of the cylindrical parts including an inner surface presenting the inner diameter and extending circumferentially around a center axis and longitudinally between opposite ends;
   disposing a mirror in the cylindrical part at a predetermined and fixed position along the center axis;
   disposing a mirror surface of the mirror at an angle and in a fixed position on the center axis relative to the inner surface;
   directing light to the inner surface of the cylindrical part;

reflecting the light between the mirror and the inner surface;

disposing a lens of a camera outwardly of the cylindrical part for acquiring images of the inner surface;

acquiring a plurality of images of the inner surface of the cylindrical part while the cylindrical part rotates 360 degrees about the center axis;

maintaining the mirror surface and the lens in a fixed position while acquiring the images of the inner surface and while the cylindrical part rotates 360 degrees about the center axis and moves longitudinally along the center axis until the camera acquires images of the entire inner surface between the opposite ends of the cylindrical part;

repeating said steps for each of the cylindrical parts having different inner diameters;

fixing a sum of the distance between the camera and the mirror and the distance between the mirror and the inner surface; and maintaining the sum of the distances the same while the camera acquires images of the inner surfaces of each of the cylindrical parts having different inner diameters.

11. A method as set forth in claim 10 wherein said acquiring a plurality of images includes for each image acquiring a line of single pixels.

12. A method as set forth in claim 11 including acquiring each of the images at a predetermined circumferential location along the circumference of the inner surface and a predetermined longitudinal position along the inner surface of the cylindrical part; arranging each of the images according to the predetermined circumferential locations and longitudinal positions; and generating an unwrapped display of the inner surface of the cylindrical part including the arranged images.

13. A method as set forth in claim 12 including automatically identifying defects on the inner surface of the cylindrical part using an image processing algorithm of the line images.

14. A method as set forth in claim 10 including rotating the cylindrical part 360 degrees about the center axis in a first predetermined longitudinal position along the center axis during said acquiring the images step.

15. A method as set forth in claim 14 including acquiring each of the images at a predetermined circumferential location around the circumference of the inner surface during said rotating step.

16. A method as set forth in claim 15 including moving the cylindrical part a predetermined distance longitudinally along the center axis to a second predetermined longitudinal position after said acquiring the images at the first predetermined longitudinal position.

17. A method as set forth in claim 16 including repeating said acquiring and said rotating and said moving steps until images are acquired for the entire inner surface of the cylindrical part.

18. A method as set forth in claim 10 including repeating said steps for each of the cylindrical parts.

19. A method as set forth in claim 10 including fixing the position of the camera relative to the mirror.

20. A method as set forth in claim 10 including cleaning the inner surface of the cylindrical part before said acquiring the images step.

21. A method as set forth in claim 10 wherein the fixed mirror surface does not rotate around the center axis.

22. A method as set forth in claim 10 wherein the camera remains in a fixed position while repeating said steps for each of the cylindrical parts.

23. A method as set forth in claim 10 including maintaining the light source in a fixed position while acquiring the images of the inner surface and while the cylindrical part rotates 360 degrees about the center axis and moves along the center axis until the camera acquires images of the entire inner surface between the opposite ends of the cylindrical part.

\* \* \* \* \*